(12) United States Patent
Hoffman (10) Patent No.: US 7,806,921 B2
(45) Date of Patent: Oct. 5, 2010

(54) MONOCUSP VALVE DESIGN

(75) Inventor: Grant T. Hoffman, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 104 days.

(21) Appl. No.: 12/265,188

(22) Filed: Nov. 5, 2008

(65) Prior Publication Data

US 2009/0125104 A1 May 14, 2009

Related U.S. Application Data

(60) Provisional application No. 60/986,447, filed on Nov. 8, 2007.

(51) Int. Cl.
*A61F 2/06* (2006.01)
(52) U.S. Cl. .................. 623/1.24; 623/1.11; 623/1.15
(58) Field of Classification Search ............. 623/1.15, 623/1.24, 2.1–2.19, 2.33, 2.42
See application file for complete search history.

(56) References Cited

U.S. PATENT DOCUMENTS

| | | | |
|---|---|---|---|
| 5,607,465 A * | 3/1997 | Camilli .................... | 623/1.24 |
| 5,957,949 A | 9/1999 | Leonhardt et al. | |
| 6,245,102 B1 | 6/2001 | Jayaraman | |
| 6,508,833 B2 | 1/2003 | Pavcnik et al. | |
| 7,670,368 B2 * | 3/2010 | Hill et al. .................... | 623/1.24 |
| 2004/0193253 A1 * | 9/2004 | Thorpe et al. ............... | 623/1.24 |
| 2005/0137676 A1 * | 6/2005 | Richardson et al. ........ | 623/1.11 |
| 2005/0234546 A1 * | 10/2005 | Nugent et al. .............. | 623/2.11 |
| 2005/0273159 A1 | 12/2005 | Opie | |
| 2006/0095115 A1 * | 5/2006 | Bladillah et al. ........... | 623/1.16 |
| 2006/0178728 A1 | 8/2006 | Camillie | |
| 2006/0210597 A1 | 9/2006 | Hiles | |
| 2006/0282157 A1 * | 12/2006 | Hill et al. .................... | 623/1.24 |
| 2007/0021826 A1 * | 1/2007 | Case et al. .................. | 623/1.15 |
| 2007/0093887 A1 | 4/2007 | Case et al. | |
| 2009/0105813 A1 * | 4/2009 | Chambers et al. .......... | 623/2.12 |

OTHER PUBLICATIONS

Written Opinion of the Internation Searching Authority, for International Application Number PCT/US2008/083870, Jun. 3, 2010, pp. 1-9.

* cited by examiner

*Primary Examiner*—David Isabella
*Assistant Examiner*—Seema Swaminathan
(74) *Attorney, Agent, or Firm*—Buchanan Intellectual Property Office LLC (57) ABSTRACT

The disclosure relates to implantable prosthetic valves comprising support frames. The support frames may include a plurality of symmetrically arrayed interconnected U-shaped member structures. Preferred support frames are tubular structures enclosing a longitudinal axis and including a plurality of U-shaped member structures facing a distal or a proximal end of the support frame. Each U-shaped member structure may be connected to a single longitudinally adjacent U-shaped member facing in an opposite longitudinal direction, as well as two laterally adjacent U-shaped members.

19 Claims, 6 Drawing Sheets

MONOCUSP VALVE DESIGN

PRIORITY CLAIM

This application claims the benefit of provisional U.S. Patent Application Ser. No. 60/986,447, filed Nov. 8, 2007, which is incorporated herein by reference in its entirety.

TECHNICAL FIELD

The present disclosure relates to implantable prosthetic valves having support frames adapted for percutaneous implantation within a body vessel, as well as methods of treatment pertaining to the implantation of the prosthetic valves.

BACKGROUND OF THE DISCLOSURE

Intraluminally implantable frames are being implanted in increasing numbers to treat a variety of conditions and are coming into greater use in a variety of fields. Frames implanted in vessels, ducts or channels of the human body can form part of a valve to regulate fluid flow within a body lumen or as scaffolding to maintain the patency of the vessel, duct or channel lumen. Implantable frames can also support a valve or valve leaflets for regulating fluid flow within a body lumen or for dilating a body lumen. One or more flexible valve leaflets can be attached to an implantable frame to form a medical device useful as an artificial valve. A variety of other implantable prostheses, such as stents, grafts and the like, also comprise an implantable frame placed within the body to improve the function of a body lumen.

The venous system includes a series of valves that function to assist the flow of blood returning to the heart. These natural valves are particularly important in the lower extremities to prevent blood from pooling in the lower legs and feet. Pooling of blood in the venous system may occur during certain situations, such as standing or sitting, when the weight of the column of blood in the vein can act to prevent positive blood flow toward the heart. This condition, commonly known as chronic venous insufficiency, is primarily found in individuals in which gradual dilation of the veins, thrombotic events, or other conditions prevent the leaflets of the native valves from closing properly. The failure of native valves to close properly can worsen, leading to significant leakage of retrograde flow such that the valve can become incompetent. Chronic venous insufficiency is a condition in which the symptoms can progress from painful edema and unsightly spider or varicose veins to skin ulcerations. Elevation of the feet and compression stocking can relieve symptoms, but do not treat the underlying disease. Untreated, the disease can impact the ability of individuals to perform in the workplace or maintain their normal lifestyle.

One promising approach to treating venous valve insufficiency includes the implantation of radially-expandable artificial valves placed using minimally-invasive techniques. Recently, the development of artificial and biological valves has been employed in an attempt to return normal pressure to the veins. These valves are generally designed to allow normal flow of blood back to the heart, while preventing retrograde flow. For example, U.S. Pat. No. 6,508,833 discloses a multiple-sided medical device comprising a closed frame of a single piece of wire or other resilient material and having a series of bends and interconnecting sides. A flexible covering of fabric or other flexible material may be attached to the frame to form an artificial valve. The flexible material utilized in these valves can comprised collagenous submucosa obtained from various animals, such as, pigs, cattle, and sheep. This material can be processed and preserved so as to be capable of inducing host tissue proliferation, remodeling, and regeneration of appropriate tissue structures, e.g., veins upon implantation in vivo (see, e.g., U.S. Pat. No. 6,485,723). The preparation of submucosal material is generally described in U.S. Pat. Nos. 4,902,508 and 5,554,389. The submucosal material can be prepared in large, flat sheets, which are subsequently cut and attached to a framing element, for example a stent, for deployment in a vein.

Dynamic fluctuations in the shape of the lumen of a body vessel, such as a vein, pose challenges to the design of implantable devices that conform to the interior shape of the body vessel. The shape of a lumen of a vein can undergo dramatic dynamic change as a result of varying blood flow velocities and volumes there through. Such dynamic change presents challenges for designing implantable intraluminal prosthetic devices that are compliant to the changing shape of the vein lumen. In addition, blood flow within a vein is intermittent and bidirectional, and subject to constant fluctuation in pressure and volume. These conditions in a vein present challenges to designing an implantable frame suitable for placement inside the vein. On one hand, an implantable frame lacking sufficient radial strength may fracture under repeated fluctuations of the vein diameter. On the other hand, an implantable frame with undesirably high levels of radial strength may lack flexibility and may damage the vein by failing to compress in response to normal fluctuations in the vein diameter. Likewise, an implantable frame with a high surface area contacting the interior wall of a vein may induce trauma in the vein wall, while an implantable frame with an insufficient surface area may lack sufficient durability.

Hence, what is needed is an intraluminally-placed medical device, such as an artificial valve or support frame, that is configured to create more desirable flow patterns around a valve within a body. For instance, more desirable flow patterns would circulate the blood or bodily fluids and reduce the likelihood of stagnation and the potential thrombotic conditions. Implantable devices configured to form a sinus region proximate to a valve orifice within a body vessel can create beneficial fluid flow conditions. These conditions, such as more turbulent flow, increased velocity of flow, larger and/or more numerous vortices, other factors, or a combination of the above, can mitigate the incidence of thrombosis formation near the implantable medical device.

There remains a need, therefore, for prosthetic valves having a support frame configured with a radial strength to maintain patency of a body vessel while supporting a means for regulating fluid within the body vessel and minimizing irritation to the body vessel after implantation.

SUMMARY

Implantable prosthetic valves comprising support frames are provided. In a first example, the support frames may include a plurality of symmetrically arrayed interconnected U-shaped member structures. For example, support frames may be tubular structures enclosing a longitudinal axis and including (2n) U-shaped member structures facing a distal or a proximal end of the support frame, where (n) is an integer of 1 or greater and preferably 1-8. Each U-shaped member structure may be connected to a single longitudinally adjacent U-shaped member facing in an opposite longitudinal direction, as well as two laterally adjacent U-shaped members. The support frames may be described with respect to a flat plan view comprising (2n) regions, such as four quadrants for a frame with an (n) value of 2. Preferably, the U-shaped members have substantially equal radii of curvature. The support frame may be formed from any biocompatible material, such as a shape memory metal or stainless steel.

In a second example, prosthetic valve devices are provided. The prosthetic valve preferably includes a means for regulating fluid flow in a body vessel. The prosthetic valve may be a venous valve having a flexible leaflet with a vessel-engaging portion. The one or more leaflets attached to the support frame may be formed from an extracellular matrix material or a portion of an explanted tissue valve. The second example also provides delivery systems including a prosthetic valve device and device for deploying the prosthetic valve, such as a catheter. Suitable percutaneous deployment devices may include a balloon catheter having adaptations for selectively forcing a portion of the prosthetic valve against the vessel wall, and/or adaptations for radially expanding and contracting the support frame. The prosthetic valve device may be releasably attached to the deployment device by any suitable means including by the use of adhesives or removable elements such as removable sutures.

In a third example, methods for treating venous insufficiency are provided, wherein the method includes deploying a support frame and/or a prosthetic venous valve such as that described above so as to force the valve body against the vascular wall, and selectively attach edges of the valve body against the vascular wall, to seat the valve within the vein. In another aspect of the third example, methods for modifying blood flow in a vascular vessel are also provided.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWINGS

The medical device may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION

For the purposes of promoting an understanding of the principles of the disclosure, reference will now be made to the examples illustrated in the drawings, and specific language will be used to describe the same.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

Definitions

The terms "proximal" and "distal" will be used to describe the opposing axial ends of the inventive sheath, as well as the axial ends of various component features. The term "proximal" is used in its conventional sense to refer to the end of the apparatus (or component thereof that is closest to the operator during use of the apparatus. The term "distal" is used in its conventional sense to refer to the end of the apparatus (or component thereof) that is initially inserted into the patient, or that is closest to the patient.

It is noted that terms like "preferably," "commonly," and "typically" are not utilized herein to limit the scope of the claimed disclosure or to imply that certain features are critical, essential, or even important to the structure or function of the claimed disclosure. Rather, these terms are merely intended to highlight alternative or additional features that may or may not be utilized in a particular example of the present disclosure.

[Medical Device]

Implantable prosthetic valves comprising support frames are provided. The support frames may provide sufficient radial strength to maintain patency of a body vessel and support a means for regulating fluid within the body vessel, such as one or more valve leaflets attached to the support frame. The support frames preferably distribute stress and strain forces caused by dynamic movement of the support frame within a body vessel. A reduced area of contact between the support frame and the body vessel wall may minimize trauma to the body vessel.

The prosthetic valve also includes a suitable means for regulating fluid through the body vessel, such as one or more valve leaflets attached to the support frame or a portion of an explanted tissue valve configured to function as the means for regulating fluid. The support frame may also be configured to provide sufficient rigidity and form to one or more attached structures. This permits these attached structures to function as a means for regulating fluid through the body vessel. For example, a flexible biocompatible material may be configured as a valve leaflet and attached to a portion of the support frame in a manner providing sufficient shape and form to the attached material to permit the attached material to function as a valve leaflet regulating fluid flow through a body vessel.

The support frames, and prosthetic valves comprising the support frames, are also preferably radially expandable from a radially compressed configuration to a radially expanded configuration. The support frame or valve in the radially compressed configuration is preferably sized and shaped for introduction to a body vessel within a catheter based delivery system, preferably using a catheter sized for placement within the human or animal vasculature. The radially expanded configuration may be sized and shaped for permanent placement within a body vessel, such as a vein, at an intended point of treatment.

Implantable Support Frames

Figure 1A:
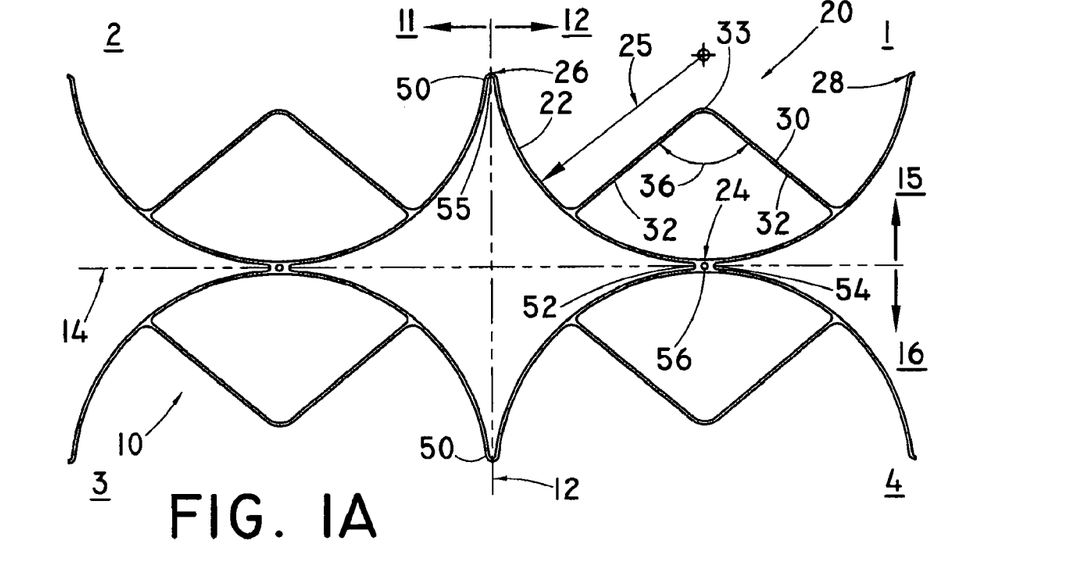
FIG. 1A is a flat plan view of one example of a four quadrant frame.
Figure 2A:
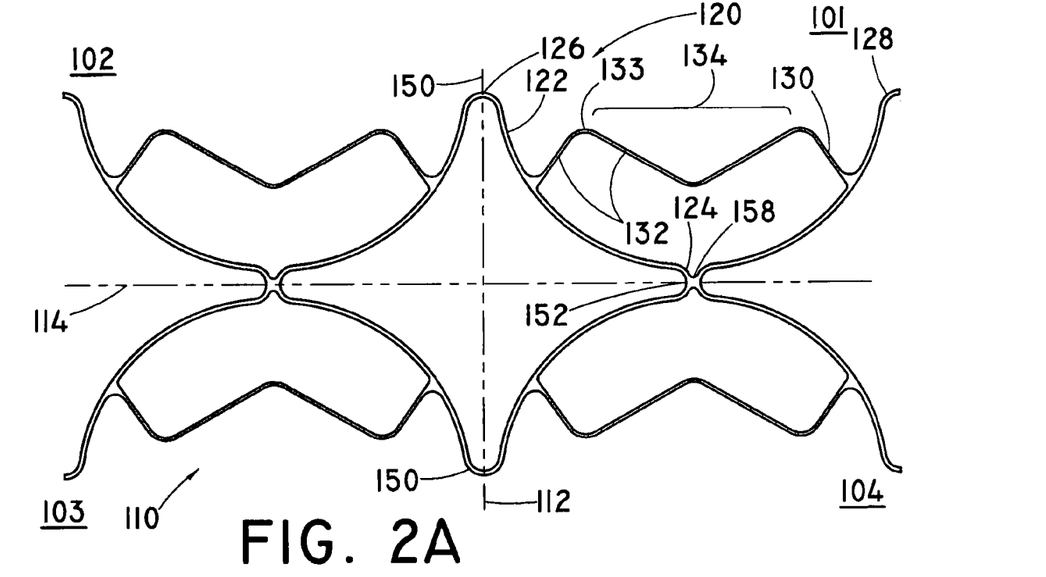
FIG. 2A is a first flat plan view of another example of a four quadrant frame.

In a first example, implantable support frames are provided. The support frames can be illustrated with respect to the following examples, which serve to illustrate certain preferred aspects of the first example of the disclosure. FIGS. 1A and 2A are flat plan views of two different examples of cylindrical support frames according to the first example. The cylindrical support frames may be obtained from the pattern shown in each flat plan view by cutting the pattern from either a cylindrical tube of the support frame material, or from a flat piece of the support frame material which is then rolled and joined to form the support frame by any suitable method. Methods of cutting the flat plan pattern into the support frame material include laser cutting and chemical etching. Preferably, the support frames are cut from a tube or cannula of shape memory metal to provide a radially self-expanding support frame. When forming the support frame from shape memory metal such as nitinol, the support frame can be laser cut from a nitinol tube. Thereafter, the support frame can be subjected to a shape-setting process in which the cut tube is expanded on a mandrel and then heated. Multiple expansion and heating cycles can be used to shape-set the support frame to the final expanded diameter. Preferably, the final expanded diameter is equal to the desired deployed diameter of the support frame. During expansion, the support frame is preferably axially restrained such that the length of the support frame does not change during expansion. The finished support frame preferably has an austenite finish temperature less than body temperature. Thus, at body temperature, the support frame will self-expand to the desired deployed diameter due to the shape memory characteristic of the metal forming the support frame.

FIG. 1A is a flat plan view of a first support frame 10. The first support frame 10 is symmetrical about a longitudinal axis 12 and a latitudinal axis 14, the intersection of which forms four quadrant 20 regions of the frame. The support frame 10 is divided into each quadrant 20 by the longitudinal axis 12 and the latitudinal axis 14. The longitudinal axis 12 bisects the frame 10 between a left side region 11 and a right side region 13. The latitudinal axis 14 bisects the frame 10 into a distal side region 15 and a proximal side region 16. Each quadrant 20 is labeled in FIG. 1A according to a left or right side region and a proximal and distal side region. Thus, a first quadrant 1 region may be identified at the right, distal side of the flat plan view of the frame 10; a second quadrant 2 may be identified at the left, distal side of the flat plan view; a third quadrant 3 may be identified at the left, proximal side of the flat plan view; and a fourth quadrant 4 may be identified at the right, proximal side of the flat plan view. Each quadrant 20 comprises a U-shaped member 22. The U-shaped member 22 has a bight 24 and a first end point 26 and a second end point 28 opposite the first end point 26. Each bight 24 has a first radius 25 and forms the inflection point of the curvature extending from the first end point 26 to the second end point 28, which is characterized by the first radius 25.

Preferably, the frame 10 includes a symmetrically disposed U-shaped member 22 in each quadrant 20 of the flat plan view. The first radius 25 of the bight 24 of the U-shaped members are preferably congruent and substantially equal, although other aspects of the first example provide frames including two or more U-shaped members 22 and/or bight 24 structures that are incongruous and have a different radius of curvature.

The U-shaped member 22 optionally includes one or more supporting arm 30 structure(s) transversing the U-shaped member 22. The supporting arm 30 can be in a variety of sizes, shapes and patterns. If more than one supporting arm is present, each arm can be a different size, shape and pattern. Referring to FIG. 1A, the support frame 10 in this example includes a single supporting arm 30 comprising two interconnected struts 32 connected by a bend 33 of about 90 degrees 36.

Figure 1B:
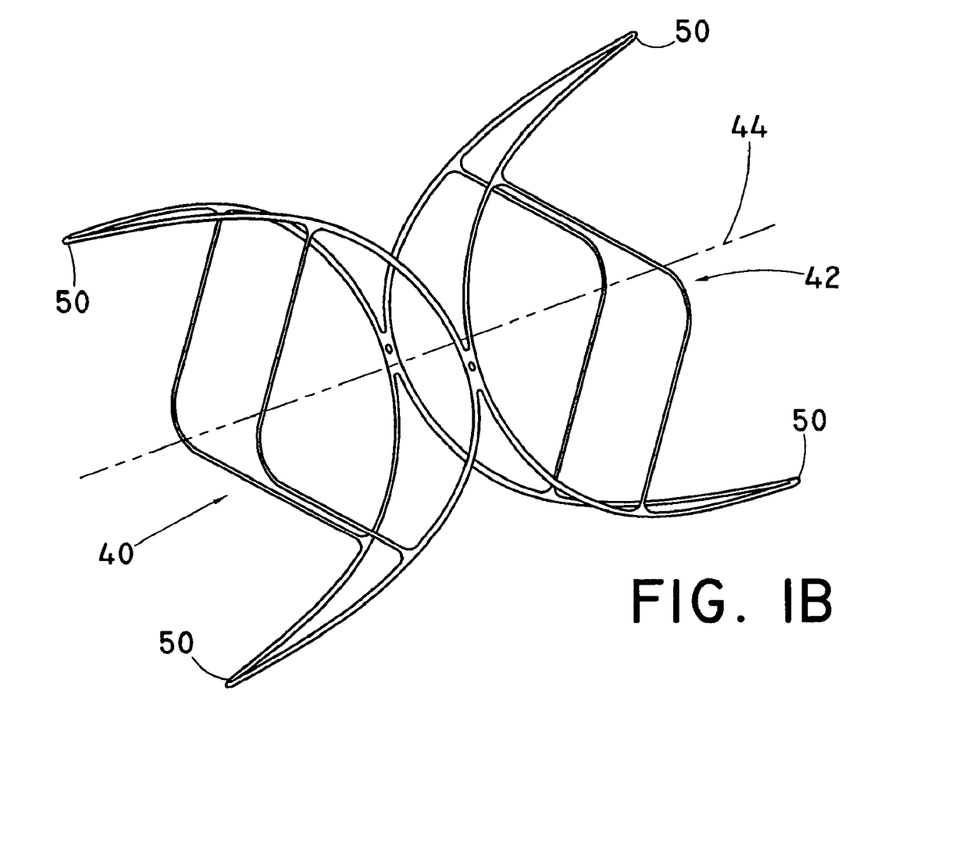
FIG. 1B is a perspective view of the four quadrant frame of FIG. 1A formed as a tubular structure.
Figure 1C:
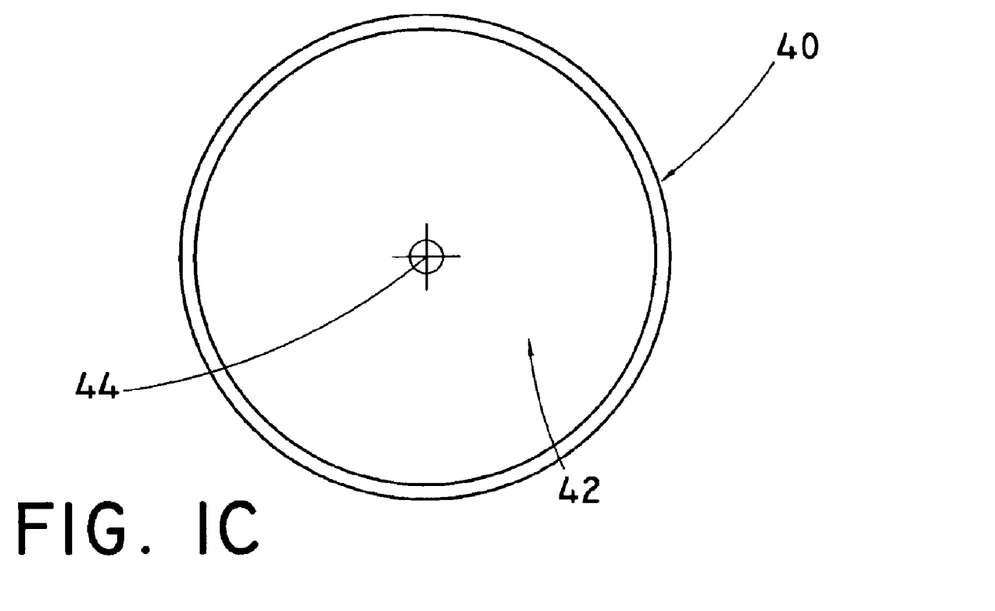
FIG. 1C is an end view of the lumen of the tubular structure formed from the four quadrant frame of FIG. 1A.

The flat plan view of FIG. 1A may be used to form a corresponding a tubular support frame structure 40 as shown in FIG. 1B, for example by laser cutting the pattern of the flat plan view into a cannula of biocompatible material. The tubular structure defines a lumen 42 with a longitudinal axis 44 at the center of the lumen 42. FIG. 1C is an end view of the tubular support frame 40 shown in FIG. 1B. Upon implantation, the longitudinal axis 44 is substantially parallel to a body vessel when the body vessel. The tubular structure 40 includes four interconnected U-shaped member 22 structures from each quadrant 20 of the flat plan view of FIG. 1A. Each of the four U-shaped member 22 structures is symmetrically connected to two other congruent U-shaped member 22 structures at a first connection 50 and a second connection 52.

Preferably, the frame 10 in the tubular configuration shown in FIG. 1B includes a total of (2n) U-shaped member 22 structures each joined to one longitudinally adjacent congruent U-shaped member 22 structure and one laterally adjacent congruent U-shaped member 22 structure, where (n) is an integer. More preferably, (n) of the U-shaped member 22 structures open in a proximal longitudinal direction and (n) of the U-shaped member 22 structures open in a distal longitudinal direction. The plurality of U-shaped member 22 structures is preferably substantially similar or identical in structure, preferably having a degree of similarity to provide a desired level of radial strength to the frame 10. Most preferably, the (2n) U-shaped member 22 structures are interconnected to no more than two other adjacent U-shaped member 22 structures. For example, a frame comprising (2n) U-shaped member 22 structures preferably includes (2n) first connection points defined between laterally adjacent U-shaped member 22 structures and (n) second connection points between longitudinally adjacent U-shaped member 22 structures. Preferably, the integer (n) is 1-8, including frames with n=1, 2, 3, 4, 5, 6, 7 and 8 and all of the second connection points are positioned at different radial positions around a common position along the longitudinal axis. In the frame 10 shown in FIGS. 1A and 1B, the integer (n) is equal to 2, and the frame includes four first connections 50 and two second connections 52. In the tubular frame structure 40 shown in FIG. 1B, two pairs of first connections 50 are disposed in a radially symmetric fashion about the longitudinal axis 44 at both the proximal end and the distal end of the frame 10. Each pair of first connections 50 are positioned at the same longitudinal position along the longitudinal axis 44. The second connections 52 shown in FIG. 1B are positioned radially opposite one another across the lumen 42. While each of the second connections 52 may be positioned at the same or different radial positions with respect to the longitudinal axis 44, each second connection 52 is preferably longitudinally aligned at the same position along the longitudinal axis 44.

Figure 1D:
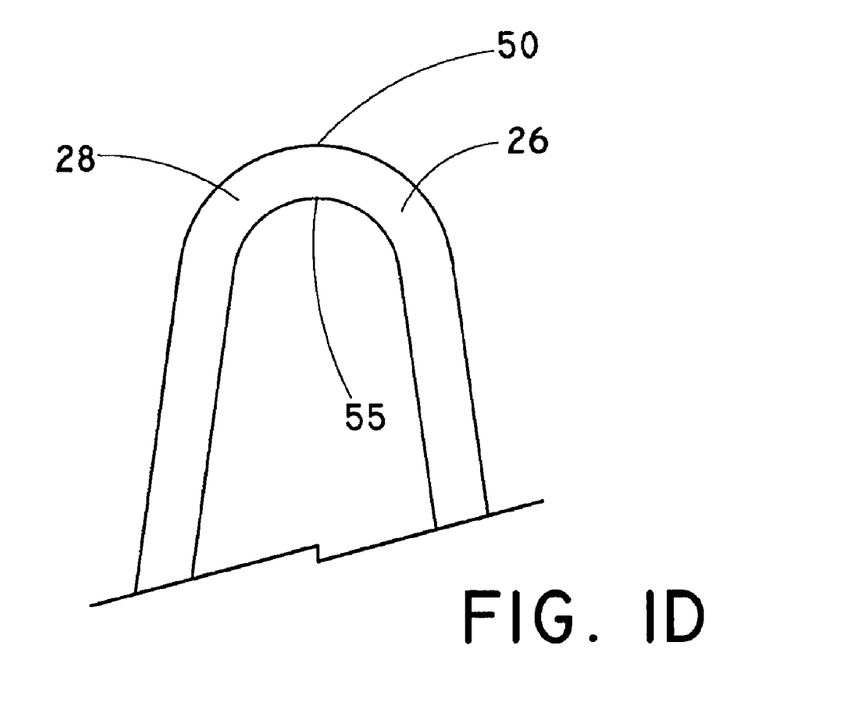
FIG. 1D is a view of second radius of the first connection of one example of the four quadrant frame of FIG. 1A.

In the frame 10, the first connection 50 may be defined between a first end point 26 of each U-shaped member 22 and a second end point 28 of the laterally adjacent U-shaped member 22. Referring to FIG. 1D, the first connection 50 may be configured as a rounded bend having a second radius 55, or as a pointed joining of terminal portions of laterally adjacent U-shaped member 22 structures. The second radius 55 may be less than the first radius 25 of the bight 24. However, the second radius 55 may alternatively be substantially less than, even at least one order of magnitude less than, the first radius 25 of the bight 24.

The second connection 52 may be defined between the bight 24 of each U-shaped member 22 and the bight 24 of the longitudinally adjacent U-shaped member 22. Optionally, the second connection 52 may be a strut segment extending between the bight 24 portion of longitudinally adjacent U-shaped member 22 structures. For example, the frame 10 can further comprise a joining member 54 at the second connection 52 as shown in FIGS. 1A and 1B. The joining member 54 extends between the bight 24 of each U-shaped member 22 and the bight 24 of the adjacent U-shaped member 22. For example, the joining member 54 extends between: (i) the bight 24 of the U-shaped member 22 of the first quadrant 1 and the bight 24 of the adjacent U-shaped member 22 of the fourth quadrant 4; and (ii) the bight 24 of the U-shaped member 22 of the second quadrant 2 and the bight 24 of the adjacent U-shaped member 22 of the third quadrant 3. Optionally, the joining member defines an orifice 56 between the longitudinally adjacent bight 24 portions of two U-shaped member 22 structures.

In the frame 10 shown in FIGS. 1A and 1B, the first connections 50 are formed between: (i) the first end point 26 of the U-shaped member 22 of the first quadrant 1 and the second end point 28 of the adjacent U-shaped member 22 of the second quadrant 2; (ii) the first end point 26 of the U-shaped member 22 of the second quadrant 2 and the second end point 28 of the U-shaped member 22 of the first quadrant 1; (iii) the first end point 26 of the U-shaped member 22 of the fourth quadrant 4 and the second end point 28 of the adjacent U-shaped member 22 of third quadrant 3; and (iv) the first end point 26 of the U-shaped member 22 of the third quadrant 3 and the second end point 28 of the U-shaped member 22 of fourth quadrant 2. Likewise, the second connections 52 are between: (i) the bight 24 of the U-shaped member 22 of the first quadrant 1 and the bight 24 of the adjacent U-shaped member 22 of the fourth quadrant 4; and (ii) the bight 24 of the U-shaped member 22 of the second quadrant 2 and the bight 24 of the adjacent U-shaped member 22 of the third quadrant 3.

Figure 2B:
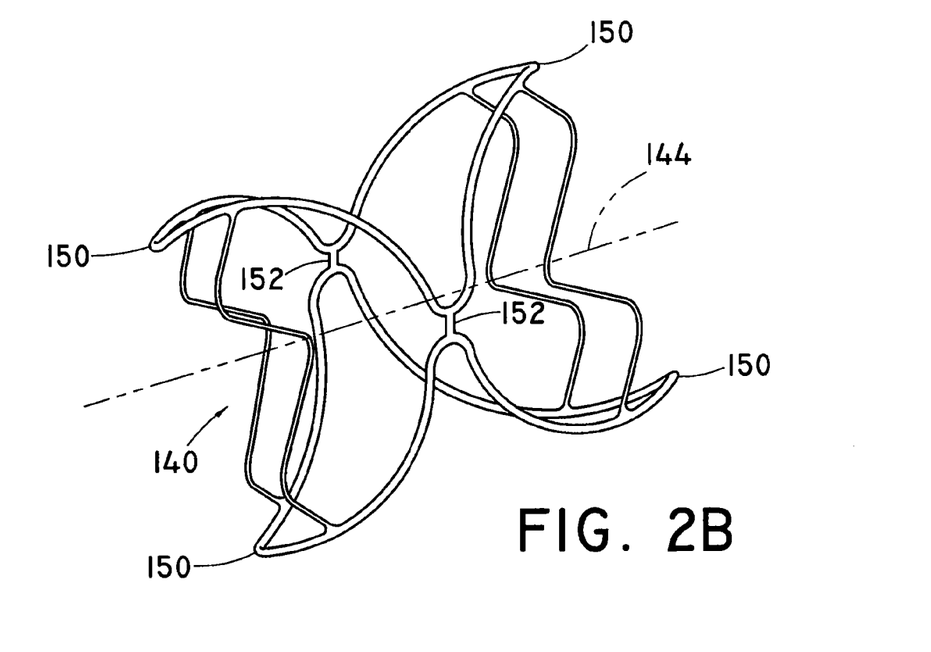
FIG. 2B is a perspective view of the four quadrant frame of FIG. 2a formed into a tubular structure.

FIGS. 2A and 2B show a second exemplary support frame of the first example in a flat plan view of FIG. 2A and a perspective view in FIG. 2B of the tubular support frame. The second support frame 110 is substantially similar to the first support frame 10, except as indicated below. The second support frame 110 is symmetrical about a longitudinal axis 112 and a latitudinal axis 114, the intersection of which forms four quadrant 120 regions of the frame. The first connection 150 may be defined between a first end point 126 of each U-shaped member 122 and a second end point 128 of the laterally adjacent U-shaped member 122.

The second connection 152 points between longitudinally adjacent U-shaped members 122 includes a protuberance 158 instead of a joining member defining an orifice. The second support frame 122 includes a plurality of second connections 152 formed between: (i) the protuberance 158 of the bight 124 of the U-shaped member 122 of a first quadrant 101 and the protuberance 158 of the bight 124 of the adjacent U-shaped member 122 of the fourth quadrant 104; and (ii) protuberance 158 of the bight 124 of the U-shaped member 122 of the second quadrant 102 and the protuberance 158 of the bight 124 of the adjacent U-shaped member 122 of the third quadrant 103.

The second frame 110 also includes four supporting arms 130 each comprising a plurality of interconnected and alternating struts 132 and bends 133 forming a zigzag pattern 134. Each supporting arm 130 spans a single U-shaped member 122 structure, and each supporting arm 130 extends from a proximal to a distal end joined to opposite sides of a U-shaped member 122 structure. In the tubular support frame configuration shown in FIG. 2B, the points where each end of a single supporting arm 130 attach to a single U-shaped member 122 structure are positioned at the same longitudinal position along the longitudinal axis 144, and are located at the same radial distance from the longitudinal axis 144.

The support frame may be formed from any suitable material. Preferred materials for four quadrant frames include those materials that can provide the desired functional characteristics with respect to mechanical load bearing, biological compatibility, modulus of elasticity, radio-opacity, or other desired properties. For some examples, the materials used to form the implantable frames can comprise a material that exhibits excellent corrosion resistance. For some examples, the material can be selected to be sufficiently radiopaque and create minimal artifacts during magnetic resonance imaging techniques (MRI). In some examples, the implantable frame can comprise a metal, a metal alloy, a polymer, or any suitable combination thereof, for example as frame with multiple layers.

Preferably, the support frames are self-expanding comprising a material capable of significant recoverable strain to assume a low profile for delivery to a desired location within a body lumen. After release of the compressed self-expanding stent, it is preferred that the frame be capable of radially expanding back to its original diameter or close to its original diameter. Accordingly, some examples provide frames made from material with a low yield stress (to make the frame deformable at manageable balloon pressures), high elastic modulus (for minimal recoil), and is work hardened through expansion for high strength. Particularly preferred materials for self-expanding implantable frames are shape memory alloys that exhibit superelastic behavior, i.e., are capable of significant distortion without plastic deformation. Frames manufactured of such materials may be significantly compressed without permanent plastic deformation, i.e., they are compressed such that the maximum strain level in the stent is below the recoverable strain limit of the material. Discussions relating to nickel titanium alloys and other alloys that exhibit behaviors suitable for frames can be found in, e.g., U.S. Pat. No. 5,597,378 (Jervis) and WO 95/31945 (Burmeister et al.). A preferred shape memory alloy is Ni—Ti, although any of the other known shape memory alloys may be used as well. Such other alloys include: Au—Cd, Cu—Zn, In—Ti, Cu—Zn—Al, Ti—Nb, Au—Cu—Zn, Cu—Zn—Sn, CuZn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. These alloys may also be doped with small amounts of other elements for various property modifications as may be desired and as is known in the art. Nickel titanium alloys suitable for use in manufacturing implantable frames can be obtained from, e.g., Memory Corp., Brookfield, Conn. One suitable material possessing desirable characteristics for self-expansion is Nitinol, a Nickel-Titanium alloy that can recover elastic deformations of up to 10 percent. This unusually large elastic range is commonly known as superelasticity.

Alternatively, the implantable frames are designed to be expanded by a balloon or some other device (i.e., the frames are not self-expanding), and may be manufactured from an inert, biocompatible material with high corrosion resistance that can be plastically deformed at low-moderate stress levels, such as tantalum. The implantable frames can be deployed by both assisted (mechanical) expansion, i.e. balloon expansion, and self-expansion means. In examples where the implantable frame is deployed by mechanical (balloon) expansion, the implantable frame is made from materials that can be plastically deformed through the expansion of a mechanical assist device, such as by the inflation of a catheter based balloon. When the balloon is deflated, the frame can remain substantially in the expanded shape. Other acceptable materials include stainless steel, titanium ASTM F63-83 Grade 1, niobium or high carat gold K 19-22. One widely used material for balloon expandable structures is stainless steel, particularly 316L stainless steel. This material is particularly corrosion resistant with a low carbon content and additions of molybdenum and niobium. Fully annealed, stainless steel is easily deformable. Alternative materials for mechanically expandable structural frames that maintain similar characteristics to stainless steel include tantalum, platinum alloys, niobium alloys, and cobalt alloys.

Optionally, the support frame may be formed from or coated with other materials, such as polymers and bioabsorbable polymers may be included in or on the implantable support frames. The support frames or portions thereof can optionally comprise material that permits identification of the position or orientation of the frame within a body passage. Radiopaque markers are advantageously positioned at one or more ends of the implantable frame to aid the physician in positioning the frame at a site inside a body vessel. For example, portions of the implantable frame can include a radiopaque material that can be identified by X-rays. For example, U.S. Pat. No. 6,409,752, issued Jun. 25, 2002 to Boatman et al., incorporated herein by reference, discloses various radiopaque materials that can be used in or on the implantable frames.

The implantable frames may be fabricated using any suitable method known in the art. Preferably, the complete frame structure is cut from a solid tube or sheet of material, and thus the frame would be considered a monolithic unit. Laser cutting, water-jet cutting and photochemical etching are all methods that can be employed to form the structural frame from sheet and tube stock. Still other methods for fabricating the complete frame structure as previously disclosed would be understood by one of skill in the art.

Alternatively, the frame can also be formed from wire using wire forming techniques, such as coiling, braiding, or knitting. By welding the wire at specific locations a closed-cell structure may be created. This allows for continuous production, i.e. the components of the implantable frame may be cut to length from a long wire mesh tube. In addition, an implantable frame is constructed from sheet, wire (round or flat) or tubing. The method of fabrication can be selected by one skilled in the art depending on the raw material used. Techniques for forming implantable frames are discussed, for example, in Dougal et al., "Stent Design: Implications for Restenosis," Rev. Cardiovasc Med. 3 (suppl. 5), S16-S22 (2002), which is incorporated herein by reference in its entirety.

In some examples, connections between the U-shaped member of each quadrant to the U-shaped member of an adjacent quadrant in mirror symmetry at the first and second connections, as well as the connection between the supporting arms and the U-shaped member and the struts and bends of the supporting arms, may be by welding or other suitable connecting means. Other connection means include the use of a binder, heat, or chemical bond, and/or attachment by mechanical means, such as pressing, welding or suturing. In addition, portions of the frame may be attached by applying a bonding coating.

A support frame can optionally be sterilized using any suitable technique known in the art, or equivalents thereto. For example, an implantable frame can be sterilized using ethylene oxide sterilization, as described in AAM/ISO 11135:1994 "Medical Devices—Validation and Routine Control of Ethylene Oxide Sterilization," incorporated herein by reference in its entirety. In some examples, a sterilized implantable frame satisfies a minimum Sterility Assurance Level (SAL) of about $10^{-6}$.

Prosthetic Valves

In a second example, prosthetic valve devices are provided. The prosthetic valve preferably includes a support frame described with respect to the first example and a means for regulating fluid through a body vessel. Preferably the prosthetic valve prosthesis devices are configured to treat incompetent or damaged cardiac or venous valves in mammals or to otherwise beneficially modify fluid flow in a bodily passage. For example, a prosthetic valve may be configured to replace or augment the function of natural venous valves operative in veins. The prosthetic venous valve preferably includes a support frame of the first example designed to resist collapsing under the contraction of the muscle present around veins by symmetrically distributing stress and strain within the frame.

Figure 3A:
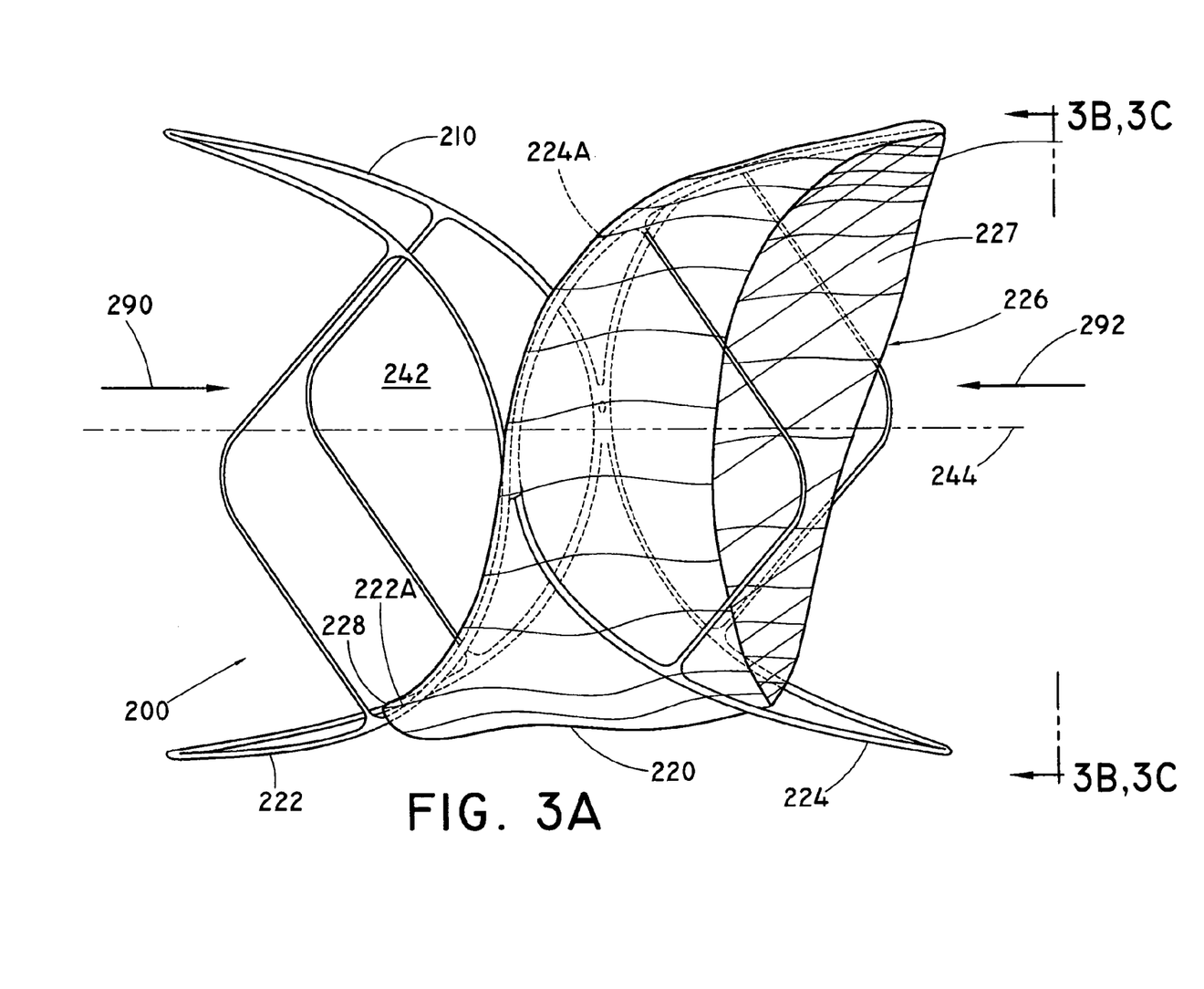
FIG. 3A is a perspective view of a prosthetic venous valve including the frame shown in FIG. 1B.
Figure 3B:
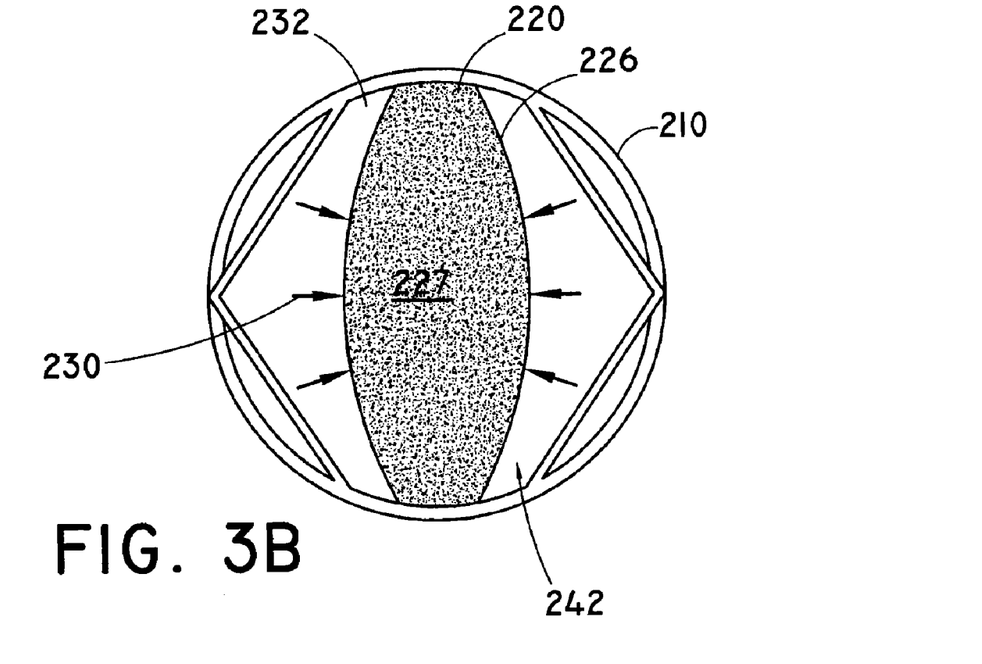
FIG. 3B is a sectional view of the prosthetic venous valve taken generally along the line A-A in FIG. 3A showing the prosthetic valve open while blood flow is in the antegrade direction.
Figure 3C:
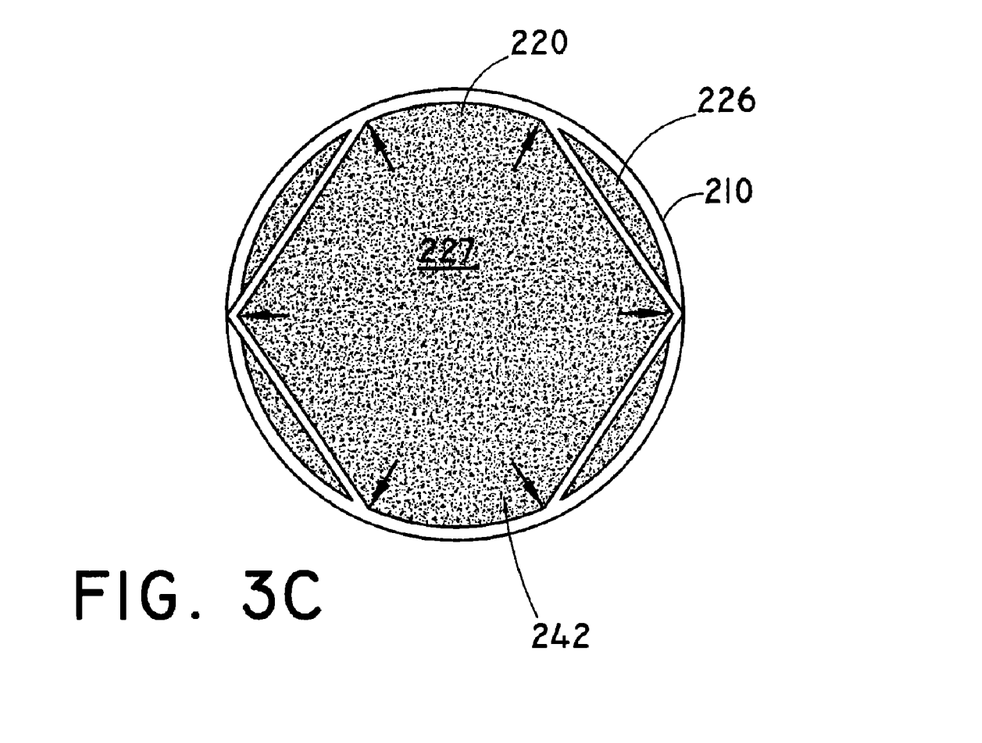
FIG. 3C is a sectional view of the prosthetic venous valve taken generally along the line A-A in FIG. 3A showing the prosthetic valve closed while blood flow is in the retrograde direction.

One non-limiting example of a suitable prosthetic valve device is shown in FIG. 3, which includes a flexible monocuspid valve member attached to a first tubular support frame described above with respect to FIG. 1B. Other prosthetic valves can be formed by attaching a means for regulating fluid flow, such as a valve leaflet or monocuspid valve member, to any support frame described according to the first example. One or more prosthetic valves can be implanted within a tubular body passage of a patient, especially a human, including for example in veins or arteries, to regulate fluid flow therein.

With reference to FIG. 3A, the prosthetic valve 200 includes a support frame 210, which is identical to the frame 10 described above with respect to the first example, except as indicated below. A monocuspid valve member 220 is attached to the support frame 210. The monocuspid valve member 220 is configured and attached in a manner to allow a portion of the monocuspid valve member 220 to extend across the lumen 242 of the support frame 210. Preferably, the support frame 210 is radially self-expanding with a maximum diameter that is slightly greater than the body vessel where the prosthetic valve 200 is implanted, such that the support frame 210 exerts sufficient outward radial force against the inner wall of the body vessel to retain the prosthetic valve 200 therein. Alternatively, the support frame may include one or more means to anchor the support frame 210 within a body vessel, such as barbs or adhesives disposed on the outer, vessel-contacting portion of the support frame 210.

In a vein, blood flow occurs in a pulsatile fashion, with surges in antegrade fluid flow occurring between intermittent retrograde fluid flow. A prosthetic venous valve 200 preferably provides a one-way valve that permits intermittent blood flow in an antegrade 290 direction while preventing the retrograde 292 fluid flow opposite antegrade direction. The monocuspid valve member 220 is a flexible structure configured to moveably traverse the lumen 242 of the support frame 210, and configured to sealably engage the opposite wall of the vein through a portion of the opposite side of the support frame 210.

As shown in FIG. 3A, the monocuspid valve member 220 may be configured as a single cone attached to a first portion 222a of a first U-shaped member 222 and a second portion 224a of a second U-shaped member 224. The monocuspid valve member 220 can be formed from a suitably flexible material to in response to fluid flow contacting the surface, and can be sized to extend transversely across the lumen 242 of the support frame 210, in a path substantially perpendicular to the longitudinal axis 244. The monocuspid valve member 220 can be oriented with the open end of the cone shape facing the direction of longitudinal retrograde 292 fluid flow through lumen 242.

For example, in a vein, the direction of retrograde 292 fluid flow is away from the heart, while antegrade 290 fluid flow proceeds along the longitudinal axis 244 in the direction toward the heart. FIG. 3B depicts a situation when subsequent antegrade blood flow occurs. Here, fluid exerts pressure 230 on a second end 228 (shown in FIG. 3A) of the monocuspid valve member 220, urging the leading edge back across the lumen 242 and forcing out fluid collected in the interior (i.e. "cup") portion 227 of the monocuspid valve member 220. As the monocuspid valve member 220 opens, the leading edge of a first end 226 is forced away from the vessel wall, opening the prosthetic valve 200 and creating regions 232 around the leaflet for unrestricted flow. These regions 232 allow blood to flow in an antegrade direction.

During retrograde 292 fluid flow, as illustrated in FIG. 3C, blood passes the leading edge along the first end 226 of the monocuspid valve member 220. However, in this scenario as blood fills the interior portion 227 of monocuspid valve member 220, the blood exerts pressure 250 urging the leading edge to transversely cross the lumen 242 and sealably engage the vein wall. The monocuspid valve member 220 may have a closed or substantially closed end and an open end. The monocuspid valve member 220 quickly fills with the retrograde flowing blood, preventing blood from flowing through the prosthetic valve 200 in the retrograde direction.

Alternatively, a multicusp leaflet configuration may be utilized, and the vascular valve device may comprise multiple leaflets configured in such a manner to allow the leaflets to co-apt within the lumen 242 of the support frame 210. The valve leaflets can have any suitable shape. Preferably, the valve leaflet includes one or more edges attached to a valve support frame 210 and extend within the lumen 242. The valve leaflets preferably have (n) edges and (n−1) edges of each valve leaflet preferably contact the support frame 210, where (n) is an integer equal to 2 or greater. Valve leaflets with (n) of 2, 3, or 4 are preferred, although leaflets with other shapes can also be used. Preferably, at least 2 edges of a valve leaflet are attached to a valve support frame 210, and at least one edge of a valve leaflet is a leaflet free edge that is not attached to any support frame.

Figure 4A:
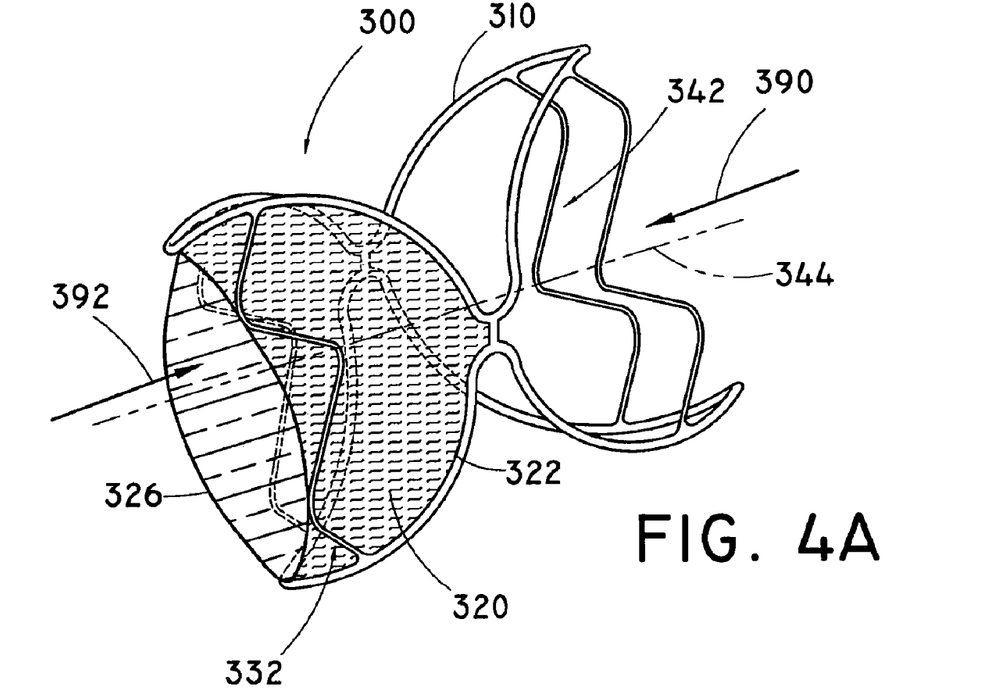
FIG. 4A is a perspective view of a second prosthetic venous valve including the frame shown in FIG. 2B.

With reference to FIG. 4A, a second prosthetic valve 300 includes a support frame 310, which is identical to the frame 140 described above with respect to the first example, except as indicated below. A monocuspid valve member 320 is attached to the support frame 310. The monocuspid valve member 320 is configured and attached in a manner to allow a portion of the monocuspid valve member 320 to extend across the lumen 342 of the support frame 310. Preferably, the support frame 310 is radially self-expanding as shown in FIG. 2B, with a maximum diameter that is slightly greater than the body vessel where the prosthetic valve 300 is implanted, such that the support frame 310 exerts sufficient outward radial force against the inner wall of the body vessel to retain the prosthetic valve 300 therein. Alternatively, the support frame may include one or more means to anchor the support frame 310 within a body vessel, such as barbs or adhesives disposed on the outer, vessel-contacting portion of the support frame 310.

In a vein, blood flow occurs in a pulsatile fashion, with surges in antegrade fluid flow occurring between intermittent retrograde fluid flow. A prosthetic venous valve 300 preferably provides a one-way valve that permits intermittent blood flow in an antegrade 390 direction while preventing the retrograde 392 fluid flow opposite antegrade direction. The monocuspid valve member 320 is a flexible structure configured to moveably traverse the lumen 342 of the support frame 310, and configured to sealably engage the opposite wall of the vein through a portion of the opposite side of the support frame 310.

Figure 4B:
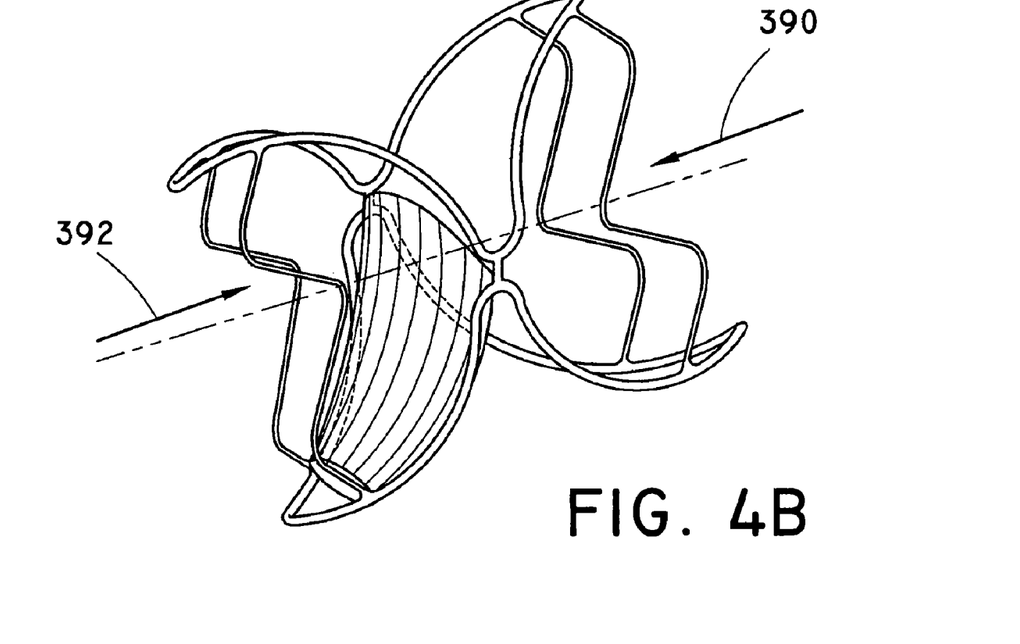
FIG. 4B is a perspective view of a second prosthetic venous valve including the frame shown in FIG. 2B.

The monocuspid valve member 320 is shown in FIG. 4A in a closed-valve configuration or FIG. 4B in an open-valve configuration. The valve member 320 may be configured as an expandable pocket attached to a first portion 322 of a first U-shaped member 322. The expandable pocket valve member 320 may be formed from explanted tissue, such as a resected portion of a tricuspid heart valve. The valve member 320 may be treated to provide a suitable flexibility and resistance to thrombgenesis. For example, the valve member 320 may be treated to induce cross-linking of the tissue (e.g., by contact with chemical crosslinking agents such as glutaraldehyde), and irradiated to soften the resulting partially cross-linked tissue. The monocuspid valve member 320 can be formed from a suitably flexible material to in response to fluid flow contacting the surface, and can be sized to extend transversely across the lumen 342 of the support frame 310, in a path substantially perpendicular to the longitudinal axis 344. The monocuspid valve member 320 can be oriented with the open end of the cone shape facing the direction of longitudinal retrograde 392 fluid flow through lumen 342. For example, in a vein, the direction of retrograde 392 fluid flow is away from the heart, while antegrade 390 fluid flow proceeds along the longitudinal axis 344 in the direction toward the heart. FIG. 3B depicts a situation when subsequent antegrade blood flow occurs. Here, fluid exerts pressure 330 on a second end 328 (not shown) of the monocuspid valve member 320, urging the leading edge back across the lumen 342 and forcing out fluid collected in the interior (i.e. "cup") portion 227 of the monocuspid valve member 320. As the monocuspid valve member 320 opens, the leading edge of a first end 326 is forced away from the vessel wall, opening the prosthetic valve 300 and creating regions 332 around the leaflet for unrestricted flow. These regions 332 allow blood to flow in an antegrade direction.

A wide variety of materials acceptable for use as a monocuspid valve member or valve leaflets are known in the art, and any suitable material can be utilized. The material chosen need only be able to perform as described herein, and be biocompatible, or able to be made biocompatible. Examples of suitable materials include natural materials, and synthetic materials.

In certain examples of the disclosure, the leaflet is formed from a flexible material comprising a naturally derived or synthetic collagenous material, and especially an extracellular collagen matrix material. Examples of suitable natural materials include collagen and extracellular matrix (ECM) material, such as submucosa. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an ECM. ECM may be isolated from submucosa (including small intestine submucosa), stomach submucosa, urinary bladder submucosa, tissue mucosa, renal capsule, dura mater, liver basement membrane, pericardium or other tissues. One specific example of ECM is small intestine submucose (SIS). When implanted, SIS can undergo remodeling and can induce the growth of endogenous tissues upon implantation into a host. SIS has been used successfully in vascular grafts, urinary bladder and hernia repair, replacement and repair of tendons and ligaments, and dermal grafts. SIS is particularly well-suited for use as valve members, such as leaflets. Suitable extracellular matrix materials ("ECM material") include, for instance, submucosa (including, for example, small intestinal submucosa ("SIS"), stomach submucosa, urinary bladder submucosa, or uterine submucosa), renal capsule membrane, dura mater, pericardium, serosa, and peritoneum or basement membrane materials, including liver basement membrane. These layers may be isolated and used as intact natural sheet forms, or reconstituted collagen layers including collagen derived from these materials or other collagenous materials may be used. For additional information as to submucosa materials useful in the present disclosure, and their isolation and treatment, reference can be made to U.S. Pat. Nos. 4,902,508, 5,554,389, 5,993,844, 6,206,931, and 6,099,567, the contents of which are incorporated herein by reference. Renal capsule tissue can also be obtained from warm blooded vertebrates, as described more particularly in copending U.S. patent application Ser. No. 10/186,150, filed Jun. 28, 2002, and International Patent Application Ser. No. PCT/US02/20499, filed Jun. 28, 2002, and published Jan. 9, 2003 as International Publication Number W003002165, the contents of which are incorporated herein by reference. In one example of the disclosure, the ECM material is porcine SIS. SIS can be prepared according to the method disclosed in U.S. 2004/0180042A1, published Sep. 16, 2004, the contents of which are incorporated herein by reference. In addition to xenogenic biomaterials, such as SIS, autologous tissue can be harvested as well. Additionally Elastin or Elastin Like Polypetides (ELPs) and the like offer potential as a material to fabricate the flexible covering or discrete shaping members to form a device with exceptional biocompatibility. Another alternative is use of allographs such as harvested native valve tissue. Such tissue is commercially available in a cryopreserved state.

In one aspect, the valve member, and preferably a valve leaflet, is formed from explanted biological tissue, such as aortic tissue, that is treated in a manner that improves the biocompatibility of the tissue for an intended use. For example, the tissue may be treated to improve resistance to post-implantation mineralization. One preferred method is described in U.S. Pat. No. 5,595,571 (Filed Apr. 18, 1994), incorporated by reference herein in its entirety, which involves exposing biological material including cellular and non-cellular structural components to a buffered solution having a pH in the range from about 5.0 to about 8.0 and a temperature in the range from about 12° C. to about 30° C. for a sufficient amount of time to facilitate the degradation of cells by autolytic enzymes within the cells, whereby at least one region of the biological material is rendered substantially acellular while preserving the overall structural integrity and non-cellular structural components of the biological material The exposure occurs prior to any fixation of the biological material. Other suitable tissue treatments are described in the following references, all of which are incorporated herein by reference in their entirety: U.S. Pat. Nos. 5,720,777, 5,843, 180 and 5,843,181 (Biological Material Pre-fixation Treatment); U.S. Pat. No. 4,798,611 (Enhancement of Xenogeneic Tissue by treatment with glutaraldehyde and then irradiation); U.S. Pat. No. 4,813,958 (Crosslinked anisotropic mammalian diaphragm in surgical reconstruction); U.S. Pat. No. 3,966,401 (Tissue for Implantation so as to Provide Improved Flexibility by Tissue subjecting tissue to tanning fluid when under pressure until the tissue assumes a natural configuration during tanning in Tanning fluids including 4% formaldehyde and 2% glutaraldehyde); U.S. Pat. No. 4,800,603 (Tissue Fixation with Vapor by subjecting tissue to a vapor of a fixative while the tissue is unstressed); and U.S. Pat. Nos. 4,813,964 and 4,813,958 (Crosslinked anisotropic xenogeneic diaphragm tissue in flexor tendon pulley reconstruction, such as a method of tissue replacement for nonfunctional flexor tendon pulleys including replacing the flexor tendon pulleys with anisotropic, crosslinked mammalian, bovine or porcine diaphragm which is characterized in that the diaphragm has one smooth side and one fibrous side, the smooth side being placed against the flexor tendon). Preferably, the explanted tissue explanted tissue is pre-treated by performing at least one of the following steps: maintaining the explanted tissue at a pH in the range from about 5.0 to about 8.0 and a temperature in the range from about 12° C. to about 30° C. for a sufficient amount of time sufficient to effect the degradation of at least a portion of the cells by autolytic enzymes within the cells; contacting the explanted tissue with a chemical cross-linking agent and then irradiating with X-ray or gamma radiation; contacting the explanted tissue with a tanning fluid including formaldehyde or glutaraldehyde; or placing tissue explanted tissue within an atmosphere of substantially unpressurized vapor of containing glutaraldehyde, and maintaining the tissue within the atmosphere of substantially unpressurized vapor in a manner sufficient to provide substantially uniform application of the fixative solution for a period of time to cause the desired fixation of said tissue.

The valve leaflet may be formed from a synthetic polymeric material. Examples of suitable polymeric materials include polyesters, such as poly(ethylene terephthalate), polylactide, polyglycolide and copolymers thereof; fluorinated polymers, such as polytetrafluroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances.

In addition, the valve leaflet material may be a biocompatible polyurethane or derivative thereof. One example of a biocompatible polyurethane is THORALON (THORATEC, Pleasanton, Calif.), as described in U.S. Patent Application Publication No. 2002/0065552 A1 and U.S. Pat. No. 4,675, 361, both of which are incorporated herein by reference. According to these patents, THORALON is a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer. The SMA-300 component (THORATEC) is a polyurethane comprising polydimethyl siloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference. The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates or pore forming agents, including inorganic salts that may be removed by contacting the material with a suitable solvent to dissolve and remove the inorganic salt after pore formation. Formation of porous THORALON is described, for example, in U.S. Pat. No. 6,752,826 and 2003/0149471 A1, both of which are incorporated herein by reference. Non-porous THORALON can be formed by mixing the polyetherurethane urea (BPS-215) and the surface modifying additive (SMA-300) in a suitable solvent, such as dimethyacetamide (DMAC). The composition can contain from about 5 wt % to about 40 wt % polymer, and different levels of polymer within the range can be used to fine tune the viscosity needed for a given process. The composition can contain less than 5 wt % polymer for some spray application examples. The entire composition can be cast as a sheet, or coated onto an article such as a mandrel or a mold to form a valve leaflet, which can be dried to remove the solvent.

The monocuspid valve member 220 or two or more valve leaflets may be securely mounted to the support frame 210 by any suitable means. The valve leaflet material can be attached to the support frame by any appropriate attachment means, including but not limited to, adhesive, fasteners, and tissue welding using heat and/or pressure. Alternatively, the valve leaflet may be formed on the support frame by an appropriate means, including but not limited to vapor deposition, spraying, electrostatic deposition, ultrasonic deposition, or dipping. One or more valve leaflets can be attached to the support frame by other methods. In one example, a sheet of material is cut to form a valve leaflet and the edges of the leaflet are wrapped around portions of a support frame and portions of the valve leaflet sealably connected together to fasten the valve leaflet around the support frame. For example, one edge of a sheet of valve leaflet material can be wrapped around a portion of the support frame and held against the body of the valve leaflet, so that the valve leaflet material forms a lumen enclosing a portion of the support frame. A small amount of a suitable solvent is then applied to the edge of the valve leaflet material to dissolve the edge into an adjacent portion of the valve leaflet material and thereby seal the material around the support frame.

In another example, the sheet of valve leaflet material is shaped to form the valve leaflet that is attached to a portion of a support frame using stitching through the valve leaflet material and around a portion of the support structure, adhesives, tissue welding or cross linking to directly join the valve leaflet material to the support frame. A valve leaflet attached to a support frame can be permitted to move relative to the support frame, or the valve leaflet can be substantially fixed in its position or orientation with respect to the support frame by using attachment configurations that resist relative movement of the valve leaflet and the support frame.

Methods of Delivery and Treatment

Artificial valve prostheses can be deployed at various locations and lumens in the body, such as, for example, coronary, vascular, nonvascular and peripheral vessels, ducts, and the like. In one example, a valve leaflet is attached to the support frame to provide an implantable valve prosthesis that can be implanted within a vein, for instance, near an incompetent venous valve to treat venous valve insufficiency. Prosthetic valve devices of the present disclosure are desirably adapted for deployment within the vascular system, and in certain preferred examples, are adapted for deployment within the venous system. Accordingly, a prosthetic valve can be adapted as a venous valve, for example, for attachment within veins of the legs or feet, to treat venous insufficiency.

The prosthetic valves described herein can be configured for delivery to a body vessel in a radially compressed configuration, and radially expanded at a point of treatment within the body vessel. The overall configuration, cross-sectional area, and length of a medical device frame having a tubular configuration (compressed or expanded) may depend on several factors, including the size and configuration of device, the size and configuration of the vessel in which the device will be implanted, the extent of contact between the device and the walls of the vessel, and the amount of retrograde flow through the vessel that is desired.

Preferably, the support frames and/or prosthetic valves described above can be radially intraluminally delivered inside the body by a catheter that supports the implantable frame in a compacted form as it is transported to the desired site, for example within a body vessel. Upon reaching the site, the implantable support frame can be expanded and securably placed within the body vessel, for example by securably engaging the walls of the body vessel lumen. The expansion mechanism may involve permitting the support frame to expand radially outward, for example, by inflation of a balloon formed in the distal portion of the catheter, to inelastically deform the stent and fix it at a predetermined expanded position in contact with the lumen wall. The expansion balloon can then be deflated and the catheter removed. In another technique, the implantable support frame is formed of a material that will self-expand after being compacted. During introduction into the body, the implantable support frame is restrained in the compacted condition. When the stent has been delivered to the desired site for implantation, the restraint is removed, allowing the implantable frame to self-expand by its own internal elastic restoring force. Once the implantable frame is located at the constricted portion of the lumen, the sheath is removed to expose the stent, which is expanded so it contacts the lumen wall. The catheter is subsequently removed from the body by pulling it in the proximal direction, through the larger lumen diameter created by the expanded prosthesis, which is left in the body.

Implantable support frames or prostheses comprising the implantable support frame can be delivered into a body lumen using a system which includes a catheter. An appropriately sized delivery catheter can be selected by one skilled in the art for a given application. For example, some examples can be delivered using a delivery catheter selected from one or more delivery catheter sizes from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 French (F) delivery catheters, or increments of 0.1 F therebetween. In some examples, a delivery catheter sized between 1 and 25 F, or preferably between about 1.5 F and 5 F can be used, preferably a 1.8 F (0.60 mm), 2.0 F (0.66 mm), 2.3 F (0.75 mm), 2.6 F (0.85 mm), 2.7 F (0.9 mm), 2.9 F (0.95 mm), or 3.3 (1.10 mm) delivery catheters.

The implantable support frames and/or prosthetic valves can be placed in any medically appropriate location for a given application. For example, in some examples, the implantable support frame can serve as part of a venous valve prosthetic and be implanted in the femoral vein, including at the proximal (groin), mid (mid section) or distal (adjacent to the knee) portions of the vein. Preferably, prosthetic valves are placed in the superficial venous system, such as the saphenous veins in the leg, or in the deep venous system, such as the femoral and popliteal veins extending along the back of the knee to the groin.

Methods of treatment preferably include the steps of loading a prosthetic valve in a radially compressed configuration into a delivery catheter, inserting the delivery catheter into a body vessel, translating the delivery catheter to a treatment site, deploying the artificial valve prosthesis by placing the artificial valve prosthesis in an expanded configuration at the treatment site to treat the subject, and withdrawing the delivery catheter from the body vessel.

Having described the disclosure in detail and by reference to specific examples thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure. It is therefore intended that the foregoing detailed description be regarded as illustrative rather than limiting, and that it be understood that it is the following claims, including all equivalents, that are intended to define the spirit and scope of this disclosure.

I claim:

1. A four quadrant frame for an artificial valve prosthesis, each quadrant comprising:
    a U-shaped member having a bight and a first end point and a second end point opposite the first end point, and
    a supporting arm transversing the U-shaped member,
    the quadrants being formed into a tubular structure defining a longitudinal axis, the tubular structure being formed by the U-shaped member of each quadrant being connected to the U-shaped member of an adjacent quadrant in mirror symmetry at a first connection and a second connection; the first connection being between the first end point of each U-shaped member and the second end point of the adjacent U-shaped member, and the second connection being between the bight of each U-shaped member and the bight of the adjacent U-shaped member.

2. The frame of claim 1, where the frame comprises a shape memory metal.

3. The frame of claim 1, where the supporting arm comprises a plurality of interconnected struts and bends forming a zigzag pattern.

4. The frame of claim 1, where the supporting arm comprises two interconnected struts connected by a bend of about 90 degrees.

5. The frame of claim 1 further comprising a joining member at the second connection, where the joining member extends between the bight of each U-shaped member and the bight of the adjacent U-shaped member.

6. The frame of claim 5, where the joining member defines an orifice between the bight of each U-shaped member and the bight of the adjacent U-shaped member.

7. The frame of claim 1, where the bight of each U-shaped member comprises a protuberance, and where the second connection is formed between the protuberance of the bight of each U-shaped member and the protuberance of the bight of the adjacent U-shaped member.

8. A four quadrant frame for an artificial valve prosthesis, each quadrant comprising:
    a U-shaped member having a bight with a first radius and a first end point and a second end point opposite the first end point; and
    a supporting arm transversing the U-shaped member;
    the quadrants being formed into a tubular structure defining a longitudinal axis, the tubular structure being formed by the U-shaped member of each quadrant being connected to the U-shaped member of an adjacent quadrant in mirror symmetry at a first connection and a second connection; the first connection being between the first end point of the U-shaped member of each quadrant and the second end point of the U-shaped member of the adjacent quadrant and forming a bend having a second radius that is less than the first radius of the bight; and the second connection being between the bight of the U-shaped member of each quadrant and the bight of the U-shaped member of the adjacent quadrant.

9. The frame of claim 8, where the second radius of the bend of the first connection is substantially less than the first radius of the bight.

10. The frame of claim 8, where the second radius of the bend of the first connection is at least one order of magnitude less than the first radius of the bight.

11. The frame of claim 8, where the frame comprises a shape memory metal.

12. The frame of claim 8, where the supporting arm comprises a plurality of interconnected struts and bends forming a zigzag pattern.

13. The frame of claim 8, where the supporting arm comprises two interconnected struts connected by a bend of about 90 degrees.

14. The frame of claim 1 further comprising a joining member at the second connection, where the joining member extends between the bight of each U-shaped member and the bight of the adjacent U-shaped member.

15. The frame of claim 14, where the joining member defines an orifice between the bight of each U-shaped member and the bight of the adjacent U-shaped member.

16. The frame of claim 8, where the bight of each U-shaped member comprises a protuberance, and where the second connection is formed between the protuberance of the bight of each U-shaped member and the protuberance of the bight of the adjacent U-shaped member.

17. An artificial valve prosthesis comprising:
    four quadrant frame, each quadrant comprising
        a U-shaped member having a bight with a first radius and a first end point and a second end point opposite the first end point; and
        a supporting arm transversing the U-shaped member;
        the quadrants being formed into a tubular structure defining a lumen with longitudinal axis, the tubular structure being formed by the U-shaped member of each quadrant being connected to the U-shaped member of an adjacent quadrant in mirror symmetry at a first connection and a second connection; the first connection being between the first end point of the U-shaped member of each quadrant and the second end point of the U-shaped member of the adjacent quadrant and forming a bend having a second radius that is less than the first radius of the bight; and the second connection being between the bight of the U-shaped member of each quadrant and the bight of the U-shaped member of the adjacent quadrant; and a valve leaflet comprising a first edge attached to the frame and a second edge attached to the frame, the valve leaflet being positioned within the lumen, where the valve leaflet prevents or permits fluid flow through the lumen.

18. The artificial valve prosthesis of claim 17, where the valve leaflet comprises a material of small intestine submucosa.

19. A radially-expandable support frame comprising (2n) U-shaped member structures each facing a distal or a proximal end of the support frame, each U-shaped member structure connected to a single longitudinally adjacent U-shaped member facing in an opposite longitudinal direction, as well as two laterally adjacent U-shaped members, where each U-shaped member has a substantially equal radius of curvature, where (n) is an integer of 1-8.

* * * * *